United States Patent [19]

Beck et al.

[11] 4,240,977

[45] Dec. 23, 1980

[54] 2-CYANOETHYL ISOCYANIDE DICHLORIDE

[75] Inventors: Gunther Beck, Leverkusen; Gerhard Dankert, Cologne; Fritz Döring, Odenthal, all of Fed. Rep. of Germany

[73] Assignee: Bayer Aktiengesellschaft, Leverkusen, Fed. Rep. of Germany

[21] Appl. No.: 67,650

[22] Filed: Aug. 17, 1979

Related U.S. Application Data

[62] Division of Ser. No. 964,049, Nov. 27, 1978.

[30] Foreign Application Priority Data

Nov. 29, 1977 [DE] Fed. Rep. of Germany ....... 2753204

[51] Int. Cl.³ ............................................ C07C 121/43
[52] U.S. Cl. ............................................ 260/465.5 R
[58] Field of Search ..................... 260/465.5 R, 566 D

[56] References Cited

U.S. PATENT DOCUMENTS

3,267,144   8/1966   Ottmann ......................... 260/566 D

FOREIGN PATENT DOCUMENTS

| 2451634 | 5/1976 | Fed. Rep. of Germany ...... 260/566 D |
| 2458826 | 6/1976 | Fed. Rep. of Germany ...... 260/566 D |
| 2458827 | 6/1976 | Fed. Rep. of Germany ...... 260/566 D |
| 1198231 | 8/1970 | United Kingdom ................ 260/566 D |

*Primary Examiner*—Joseph Paul Brust
*Attorney, Agent, or Firm*—Sprung, Felfe, Horn, Lynch & Kramer

[57] ABSTRACT

Process for the preparation of tetrachloropyrimidine, characterized in that 2-cyanoethyl isocyanide dichloride is reacted with chlorine in the gas phase in the temperature range from 200°–650° C.

1 Claim, No Drawings

2-CYANOETHYL ISOCYANIDE DICHLORIDE

This is a division of application Ser. No. 964,049, filed Nov. 27, 1978.

The present invention relates to a new process for the preparation of tetrachloropyrimidine.

The process is characterised in that 2-cyanoethyl isocyanide dichloride of the formula $$NC-CH_2-CH_2-N=CCl_2 \qquad (I)$$

is reacted with chlorine in the gas phase in the temperature range from 200° to 650° C.

In this procedure, the best yields are generally obtained when the reaction is carried out with 3 mols of chlorine per mol of (I). If smaller amounts of chlorine are reacted, tetrachloropyrimidine is likewise obtained, but in lower yields. To ensure that 3 mols of chlorine are reacted per mol of (I), in practice at least 3 mols, generally 3–4.5 mols, of chlorine are employed per mol of (I), that is to say an excess of up to 50%. An even greater excess of chlorine can indeed be used without decreasing the yield, but is uneconomic.

It has proved appropriate to carry out the process according to the invention in the presence of chlorination catalysts. Examples which may be mentioned are silicon dioxide (silica gel) and pumice, which are impregnated with $CuCl_2$ or with $FeCl_3$. However, the customary active charcoals, such as are described, for example, in Ullmanns Encyklopädie der technischen Chemie (Ullmann's Encyclopaedia of Industrial Chemistry), volume 9, page 806, are particularly preferred as the catalyst.

The amount of catalyst is preferably such that 0.05–10 ml, preferably 0.1–5 ml, of catalyst are available per gram of (I) introduced per hour.

The process according to the invention is carried out in accordance with customary techniques for gas phase chlorination reactions. The exothermic reaction is preferably carried out in a vertical flow tube, the heat evolved being removed by means of a circulating inert gas ($N_2$, $CO_2$), by means of a circulating bath liquid or using a fluidised bed, for example consisting of corundum.

Dilution of the reaction mixture, for example with nitrogen, hydrogen chloride, carbon tetrachloride or tetrachloropyrimidine, is likewise advantageous for removing the heat.

The word flow tube is to be interpreted broadly in the present case. The flow tube can be tube-like reaction chambers of various construction, for example: straight-line, spiral-shaped or curved, in which the reaction can take place at a varying rate; these also include arrangements in the form of fluidised beds. The flow rate depends on the temperature and dilution of the reaction mixture.

For carrying out the process according to the invention, (I) and chlorine and if appropriate one of the above-mentioned diluents are first introduced into a flask, preheated to about 220°–260° C., which functions as a vaporiser and from which the vaporous reactants then enter, via a bridge likewise heated to 220°–260° C. or more, into the flow tube described above, which is packed with the catalyst and in which the reaction to give tetrachloropyrimidine, which proceeds exothermically, takes place. In this procedure, the temperature range can vary between 200° and 650° C., preferably from 220° to 500° C.

In general, the gaseous tetrachloropyrimidine issuing from the flow tube is first condensed and, after the reaction has ended, is degassed at slightly elevated temperatures (about 50° C.) by applying a waterpump vacuum for a short time. The purity of the tetrachloropyrimidine, determined by gas chromatography, is in general $\geq 95\%$. If desired, tetrachloropyrimidine which is at least 99% pure according to gas chromatography can be easily isolated by fractionation on a column (boiling point$_{12}$ 108°–110° C.).

The chlorination can, of course, also be carried out continuously.

Tetrachloropyrimidine is suitable as a reactive component for the preparation of reactive dyestuffs (compare, for example, Belgian Pat. Specification No. 578,933). Furthermore, tetrachloropyrimidine is used as a fungicidal and sporicidal agent (U.S. Pat. Specification No. 3,227,612).

The 2-cyanoethyl isocyanide dichloride of the formula (I) used as the starting material is new and is likewise a subject of the invention. It is prepared as follows:

2-Cyanoethyl-formamide (II), which is accessible in a known manner (French Patent Specification No. 976,959), for example from formamide and acrylonitrile, is reacted, according to the equation

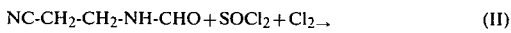

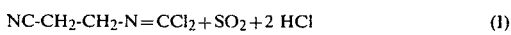

at temperatures from 40°–80° C., preferably 50°–75° C., with thionyl chloride and chloride, or a compound which splits off chlorine under the reaction conditions, preferably sulphuryl chloride.

Particularly good yields (about 90%) and high purities (up to 98%) of (I) are obtained when 2-cyanoethyl-formamide (II) is introduced into a mixture of thionyl chloride and sulphuryl chloride or chlorine in which the molar ratio thionyl chloride:sulphuryl chloride or chlorine is considerably greater than 1:1, and in general is about 3:1 to 10:1. As even higher molar ratio is possible, but has no substantial advantages.

The molar ratio of chlorine, or compound which splits off chlorine, in particular sulphuryl chloride, to (II) should be at least 1:1 in order to achieve a yield of (I) which is as high as possible. In practice, molar ratios between 1:1 and 2.5:1 are used. An even higher molar ratio is possible, but has no advantages.

It can be appropriate to introduce the 2-cyanoethyl-formamide (II) into the chlorination mixture at temperatures which are below 40°–80° C., preferably below 50°–75° C., for example between 20° and 35° C., and then only to heat the reaction mixture when, after the addition of (II) has ended, the first, slightly exothermic reaction has subsided.

The main reaction takes place between 50° and 75° C. and in general has ended after two hours at the latest.

Excess chlorinating agent, in particular excess thionyl chloride, can be used for further batches after being distilled off from the substantially less volatile 2-cyanoethyl isocyanide dichloride (I) (boiling point$_{13}$ 107° C.). The process can, of course, also be carried out continuously.

In general, the 2-cyanoethyl isocyanide dichloride (I) remaining after stripping off the excess thionyl chloride and if appropriate excess chlorinating agent, in particular sulphuryl chloride, is already of high purity (>90%) and can be employed direct in the gas phase chlorination described above. By simple distillation, in which only negligible amounts of residues which cannot be distilled remain, a (I) which is almost 98% pure according to gas chromatography is obtained in about 90% yield at boiling point$_{13}$ 107° C.

In addition to (I), the present invention also relates to the abovementioned process for its preparation.

The present invention furthermore relates to a process for the preparation of tetrachloropyrimidine, which is characterised in that 2-cyanoethyl-formamide (II) is first reacted with a mixture of thionyl chloride and chlorine, or a compound which splits off chlorine under the reaction conditions, in particular sulphuryl chloride, at temperatures from 40°–80° C., preferably 50°–75° C., to give 2-cyanoethyl isocyanide dichloride (I), and this is then reacted, appropriately without intermediate isolation, with chlorine in the gas phase in the temperature range from 200° to 650° C., preferably 220° to 500° C.

EXAMPLE 1

123 g (0.815 mol) of 2-cyanoethyl isocyanide dichloride and 231 g (3.25 mols) of chlorine are simultaneously introduced, by means of a metering pump and a flow meter respectively, in the course of 95 minutes into a 500 ml three-necked flask functioning as a vaporiser, which is heated by an oil bath at 240° C. and is provided with a bridge heated to 240° C. by means of an electric heating tape. The bridge is connected to a vertical flow tube (length 300 mm, diameter 30 mm), heated to 240° C. by an electrical coil, which is packed with active charcoal having a particle diameter of 2–3 mm (contact volume 185 ml) and in which the gas mixture produced in the vaporiser is reacted. In order to remove the heat of reaction, the flow tube is surrounded, in the manner of a Liebig condenser, by an outer jacket through which an inert gas is passed.

A thermocouple introduced coaxially into the flow tube monitors the contact temperature of 240° C. A 2 liter two-necked flask cooled by means of an ice-water bath serves as a receiver, in which the reaction product is condensed and through the second outlet of which the hydrogen chloride formed and if appropriate excess chlorine are removed.

After the reaction has ended, the condensate is degassed at 50° C. under a waterpump vacuum for a short time. Weight: 175 g. Analysis by gas chromatography gave a tetrachloropyrimidine content of 96% (corresponding to 168 g); this corresponds to a yield of 94.6% of theory.

EXAMPLE 2

In the apparatus of Example 1, 130 g (0.86 mol) of 2-cyanoethyl isocyanide dichloride are vaporised at 240° C. in the presence of 244 g (3.44 mols) of chlorine in the course of 50 minutes and the gas mixture is passed through the flow tube. An inert gas is passed through the outer jacket of the flow tube at a rate such that the contact temperature is kept between 240° and 260° C.

After working up the mixture analogously to Example 1, 180 g of condensate are obtained with a tetrachloropyrimidine content, determined by gas chromatography, of 95.9% (corresponding to 172.6 g); this corresponds to a yield of 92% of theory.

EXAMPLE 3

In the apparatus of Example 1, 453 g (3.0 mols) of 2-cyanoethyl isocyanide dichloride are vaporised at 260° C. in the presence of 900 g (12.67 mols) of chlorine in the course of 50 minutes, and the gas mixture is passed, via the bridge heated to 350° C., through the flow tube. For better removal of the heat, a glass tube sealed at the bottom by melting, and having a diameter of about 19 mm, is introduced coaxially into the flow tube so that the catalyst bed is annular over its entire length. The volume of the 5–6 mm wide ring is about 132 ml. An inert gas is passed through the outer jacket of the flow tube at a rate such that the contact temperature is kept between 380° and 400° C.

Working up analogously to Example 1 gives 625 g of condensate with a tetrachloropyrimidine content, determined by gas chromatography, of 94.2% (corresponding to 588 g); this corresponds to a yield of 90% of theory. Preparation of the starting material 2-cyanoethyl isocyanide dichloride:

(A) Using thionyl chloride/sulphuryl chloride;

98 g (1.0 mol) of 2-cyanoethyl-formamide are added dropwise to a stirred mixture of 200 ml (2.48 mols) of sulphuryl chloride and 1,200 ml (16.5 mols) of thionyl chloride at 22° C. in the course of half an hour, without cooling, whereupon the internal temperature rose gradually to 34° C.; a precipitate was simultaneously formed. The mixture was subsequently stirred for a further 20 minutes, whereupon the temperature fell to 30° C. The mixture was then stirred under reflux at an oil bath temperature of 90° C. for 2 hours. The precipitate dissolved at 50°–55° C., a gas being evolved. After the heating for two hours, the reflux temperature had risen to 70° C. After stripping off SOCl$_2$ in vacuo, 138 g of 2-cyanoethyl isocyanide dichloride were obtained at boiling point$_{13}$ 107° C. in a purity, determined by gas chromatography, of 97.7% (corresponding to 89% of theory). (b) Using thionyl chloride/chlorine 2,200 g (18.48 mols) of thionyl chloride are initially introduced into a 4 liter stirred apparatus and 453 g (4.62 mols) of 2-cyanoethyl-formamide are added dropwise, and at the same time 365 g (5.14 mols) of chlorine are passed in, at 55° C. in the course of 4 hours. After subsequently stirring the mixture at 55°–60° C. for about 30 minutes, the evolution of gas has largely ended. The mixture is worked up by distillation. 663 g of 2-cyanoethyl isocyanide dichloride are obtained at boiling point$_{12}$ 100°–110° C. in a purity, determined by gas chromatography, of 95% (corresponding to 95% of theory).

We claim:

1. 2-Cyanoethyl isocyanide dichloride.

\* \* \* \* \*